(12) United States Patent
Nagatomi et al.

(10) Patent No.: US 8,158,565 B2
(45) Date of Patent: Apr. 17, 2012

(54) MOLYBDENUM ALKYLXANTHATES AND LUBRICATING COMPOSITIONS

(75) Inventors: Eiji Nagatomi, Tokyo (JP); Noriaki Shinoda, Tokyo (JP); Yoshihiko Aihara, Tokyo (JP)

(73) Assignee: Shell Oil Company, Houston, TX (US)

( * ) Notice: Subject to any disclaimer, the term of this patent is extended or adjusted under 35 U.S.C. 154(b) by 288 days.

(21) Appl. No.: 12/525,350

(22) PCT Filed: Feb. 1, 2008

(86) PCT No.: PCT/EP2008/051261
§ 371 (c)(1),
(2), (4) Date: Feb. 12, 2010

(87) PCT Pub. No.: WO2008/092948
PCT Pub. Date: Aug. 7, 2008

(65) Prior Publication Data
US 2010/0144570 A1    Jun. 10, 2010

(30) Foreign Application Priority Data
Feb. 1, 2007    (JP) .................... 2007-023397

(51) Int. Cl.
C10M 135/04    (2006.01)
C10M 135/18    (2006.01)
(52) U.S. Cl. ........................ 508/443; 508/322
(58) Field of Classification Search .......... 508/433, 508/322
See application file for complete search history.

(56) References Cited

U.S. PATENT DOCUMENTS 5,126,465 A    6/1992    Greaney et al. ............. 556/61

FOREIGN PATENT DOCUMENTS

| DE | 3717143 | 12/1988 |
|----|---------|---------|
| EP | 0668342 | 8/1995 |
| EP | 0776959 | 6/1997 |
| EP | 1029029 | 8/2000 |
| EP | 1741772 | 10/2007 |
| GB | 789383 | 1/1958 |
| JP | 48056202 | 8/1973 |
| JP | 52019629 | 2/1977 |
| JP | 52106824 | 9/1977 |
| JP | 62161992 | 7/1987 |
| JP | 3495764 | 2/2004 |

(Continued)

OTHER PUBLICATIONS

Domrachev, G.A., et al: "Molybdenum disulfide formation during decomposition of organic compounds containing a molybdenum-sulfur bond", XP002475834.

(Continued)

*Primary Examiner* — Walter D Griffin
*Assistant Examiner* — Francis C Campanell

(57) ABSTRACT

The present invention provides a molybdenum pentakis-alkylxanthate having general formula (1) which is indicated below.

General Formula (1)

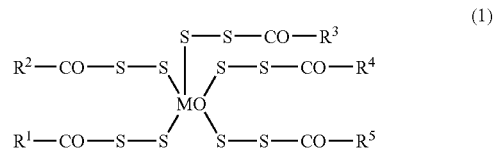

In this formula $R^1$ to $R^5$ each represent a group individually selected from linear chain or branched alkyl groups which have from 1 to 30 carbon atoms.

8 Claims, 1 Drawing Sheet

FOREIGN PATENT DOCUMENTS

| | | |
|---|---|---|
| WO | WO9721788 | 6/1997 |
| WO | WO9941332 | 8/1999 |
| WO | WO0008115 | 2/2000 |
| WO | WO0014179 | 3/2000 |
| WO | WO0014183 | 3/2000 |
| WO | WO0014187 | 3/2000 |
| WO | WO0014188 | 3/2000 |
| WO | WO0015736 | 3/2000 |
| WO | WO0118156 | 3/2001 |
| WO | WO0157166 | 8/2001 |

OTHER PUBLICATIONS

Cousins, M., et al: "Some oxo-and oxochlorocyclopentadienylmolybdenum complexes", XP002475835.

Green, Malcolm L.H., et al: Interconversion of oxo and imido ligands at a dimolybdenum center: molecular and electronic structure of [{Mo(.eta.-C5H4Me) (NPh) (.mu.-NPh)}], XP002475836.

Saurenz, Dirk, et al: "Cyclopentadienylmolybdenum(VI) and molybdenum(V) oxo chemistry: new synthetic and structural features", XP002475837.

Hogarth, Graeme, et al: "Electrochemistry of dimolybdenum complexes containing oxo, imido, and sulfide moieties. A measure of their relative .pi.-donor abilities?", XP002475838.

Bursten, Bruce E., et al: "Electronic structure of piano-stool dimmers. 8. Electronically induced conformational changes in high-valent bimetallic chalcogen complexes of the type [CpML]2(.mu.-L)2 (M=molybdenum rhenium; L=S, O)", XP002475839.

Gun, Jenny, et al: "Reduction of [(C5Me5)2Mo2O5] and [(C5Me5)2Mo2O4] in methanol/water/trifluoroacetate solutions investigated by combined on-line electrochemistry/electrospray-ionization mass spectrometry", XP002475840.

Brunner, Henri, et al: "Preparation and reactivity of binuclear oxo (pentamethylcyclopentadienyl) molybdenum sulfides", Journal of Organometallic Chemistry, 331(1), pp. 45-52, 1987, XP002475832.

Journal of Organometallic Chemistry 331(1), pp. 45-52, XP002475833.

Tanner, L.D., et al: "Structures and reactivities of cyclopentadienylmolybdenum complexes with oxo and sulfide ligands", XP002475841.

Reuter, U. et al: "On chalcogenolates. LXX. Experiments to prepare tetrathiooxalates. About alkylthio-1, 3-dithiole-2-thiones" XP002476509.

Maejima, Seiju et al: "Surface reinforcement of an inorganic porous material" XP002473509.

Unoura, Kei et al: "Substituent effects of cis-dioxobis(dithiocarbamato)molybdenum(VI) on redox properties: redox potentials for one-electron reduction and second=order rate constants for oxygen atom transfer" XP002476206.

Sovilj, S. P. et al; "Molecular modelling of new dioxomolybdenum (VI) complexes with heteroalicyclic dithiocarbamates. In Silico models for metal-implant coating within living systems" XP002476207.

Gnecco, J. A. et al: "Catalytic epoxidation of cyclohexene using molybdenum complexes" XP002476208.

Sovilj, S. P. et al: "Dioxomolybdenum (VI) complexes of methylpiperidinodithiocarboxylates" XP002476209.

Macial, Benigno et al: "An EXAFS study of Mo(VI) and Mo (V) complexes with proline dithiocarbamate" XP002476210.

Stergiou, Anagnostis C. et al: "Spectroscopic investigation of dichloro and hydrazido(2-) derivatives of bis9dithiocarbamato)dioxomolybdenum(VI) compounds. Crystal and molecular structure of bis(diisobutyldithiocarbanato) (N,N-dimethylhydrazido(2-)-N')oxomolybdenum(VI)" XP002476211.

Bhat, G. S. et al: "Synthesis and characterization of lead(II), bismuth (III), titanium(IV), selenium(IV), thorium(IV), dioxomolybdenum(VI) and dioxouranium(VI), hexamithyleniminecarbodithioate and their biological activities" XP002476212.

Nair, B. Gopalakrishnan et al: "A novel series of cis-dioxomolybdenum(VI) carbodithioate complexes" XP002476213.

Moloy, Kenneth G.: "Oxygen atom transfer reactions, Epoxide deoxygenation by bis(diethyldithiocarbamato)oxomolybdenum" XP002476214.

Berzina, S. et al: "Two-phase stability constants of some 3-pyrorolecarbodithioates and 3-indoleacrbodithioates" XP002476215.

Byr'ko, V. M. et al: "Composition and structure of mlybdenum (V, VI)5-phenyl-1-pyrazolinedithiocarbamates" XP002476216.

MOLYBDENUM ALKYLXANTHATES AND LUBRICATING COMPOSITIONS

This application is a National Stage application under 35 USC 371 of PCT/EP2008/051261, filed Feb. 1, 2008, which claims priority to Japanese Patent Application No. 2007-023397, filed Feb. 1, 2007

FIELD OF THE INVENTION

The invention relates to novel molybdenum alkylxanthates, the use thereof as friction-modifiers and lubricating compositions which contain said molybdenum alkylxanthates.

BACKGROUND OF THE INVENTION

Friction-modifiers (friction-adjusting agents) are used for adjusting the friction characteristics of a lubricant to an appropriate level. Friction-modifiers which reduce friction are used in lubricating compositions such as gear oils and engine oils with a view to reducing fuel costs. Friction-modifiers which raise friction are used for maintaining a certain high friction level in the lubricating compositions which are used in the wet-type clutch part of an automatic gear box. Many types of such friction-modifiers have been proposed.

The organic molybdenum compounds are the most typical of these friction-modifiers and, as shown in "Shinban Sekiyu Seihin Tenkasai" (New Edition, Additives for Petroleum Products), by Toshio SAKURAI, Saiwai Shobo Co., published 25 Jul. 1986, these organic molybdenum compounds are compounds which have two molybdenum atoms in one molecule as shown in formulae (2) and (3) below.

Formula (2)

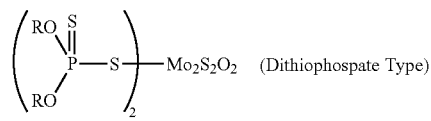
(Dithiophospate Type)

Formula (3)

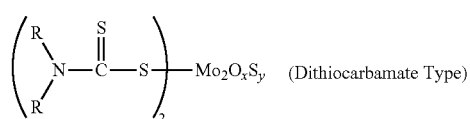
(Dithiocarbamate Type)

(Those compounds for which in this formulae x=0 and y=4, and for which x+y=4, and for which x≧2 are insoluble in oil and the others are oil-soluble.)

Furthermore, compounds in which the element molybdenum is included twice in one molecule have been disclosed in Japanese Patent No. 3495764, Japanese Examined Patent Publication 45-24562, Japanese Unexamined Patent Application Laid Open 52-19629, Japanese Unexamined Patent Application Laid Open 52-106824, and Japanese Unexamined Patent Application Laid Open 48-56202.

A problem with catalyst poisoning in the apparatus which is used for cleaning-up the exhaust gas arises when compounds which contain phosphorus in the molecule as shown in the aforementioned general formula (2) are added to engine oils and there is a demand for compounds which are phosphorus-free.

SUMMARY OF THE INVENTION

It is an object of the present invention is provide novel compounds which are useful as, for example, friction-modifiers for the optimal adjustment of friction and which do not contain phosphorus, and friction-modifiers comprising said compounds.

Another object of the invention is to provide lubricating compositions in which these compounds are used.

DETAILED DESCRIPTION OF THE PREFERRED EMBODIMENTS

Figure 1:
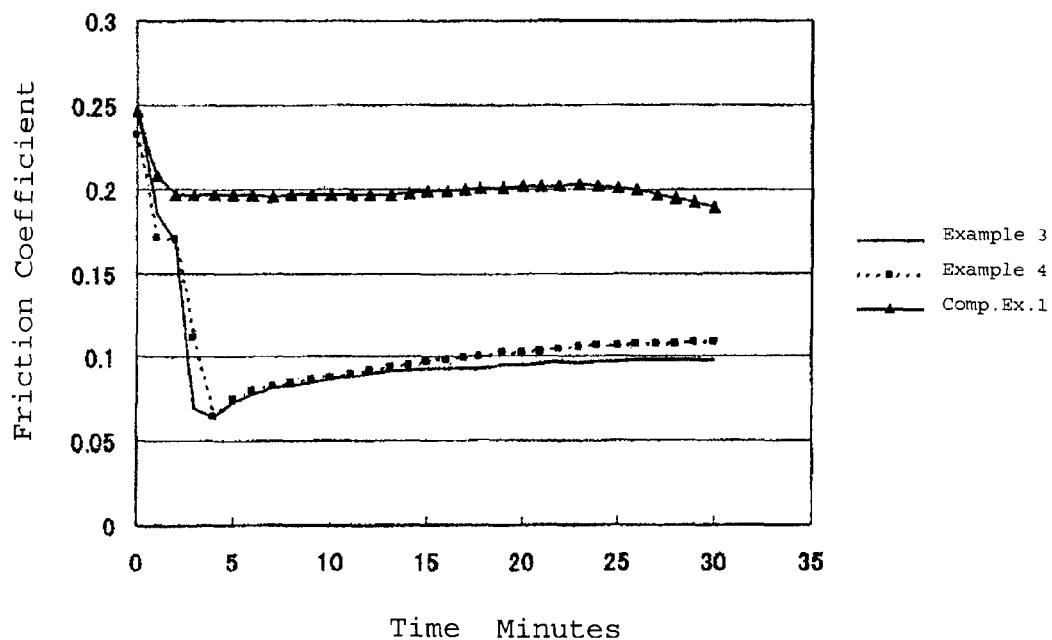
FIG. 1 shows how the friction coefficients of the lubricating oils of Examples 3 and 4 and Comparative Example 1 changed with the passage of time.

To achieve the aforementioned objects, the present invention provides molybdenum alkylxanthates which can be represented by general formula (1) which is indicated below.

General Formula (1)

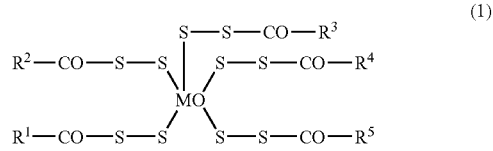
(1)

In this formula $R^1$ to $R^5$ each represent a group individually selected from the linear chain or branched alkyl groups which have from 1 to 30 carbon atoms.

Preferably, $R^1$ to $R^5$ are the same alkyl group selected from the group comprising methyl, ethyl, propyl, butyl and pentyl.

Further the present invention provides the use of the molybdenum alkylxanthates as friction-modifiers.

As the present invention provides lubricating compositions which contain the molybdenum alkylxanthates.

The compounds of this invention can be produced, for example, by means of the reactions indicated below.

(1)

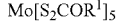

(2)

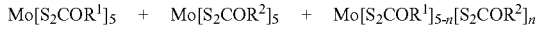

In this equation there are four types of compound ranging from that where n in $Mo[S_2COR^1]_{5-n}[S_2COR^2]_n$ is 1 to that where n is 4, and a total of six types of product is obtained in the aforementioned reaction.

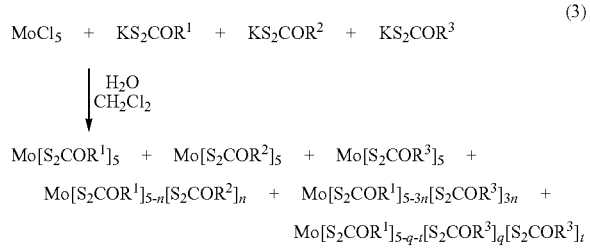

In this equation m and n are integers of value not more than 4, and there are various products ranging from that where m and n are 1 to that where m and n are 4. Also, q and t are integers of value not more than 3, and there are various products ranging from that where q and t are 1 to that where q and t are 3, and this is the same as in the case (2) above in that these are produced as a mixture by means of the aforementioned reaction.

Those where $R^1$ to $R^5$ are all the same alkyl group which has from 1 to 30 carbon atoms, preferably from 1 to 20 carbon atoms, and most desirably from 1 to 10 carbon atoms, such as a methyl group, an ethyl group, an n-propyl group, an isopropyl group, a n-butyl group, a sec-butyl group, a t-butyl group, a n-pentyl group, a 2-methylbutyl group, a n-hexyl group, a n-heptyl group, a 2-ethylhexyl group, a octyl group or the like can be cited as actual compounds of this invention, and those indicated below can be cited as actual compound names.

Molybdenum pentakis-methylxanthate, Molybdenum pentakis-ethylxanthate, Molybdenum pentakis-n-propylxanthate, Molybdenum pentakis-isopropylxanthate, Molybdenum pentakis-n-butylxanthate, Molybdenum pentakis-sec-butylxanthate, Molybdenum pentakis-t-butylxanthate, Molybdenum pentakis-n-pentylxanthate, Molybdenum pentakis-2-methylbutylxanthate, Molybdenum pentakis-n-hexylxanthate, Molybdenum pentakis-n-heptylxanthate, Molybdenum pentakis-2-ethylhexylxanthate, Molybdenum pentakis-n-octylxanthate, Molybdenum pentakis-nonanylxanthate, Molybdenum pentakis-decanylxanthate, Molybdenum pentakis-undecanylxanthate, Molybdenum pentakis-tridecanylxanthate, Molybdenum pentakis-tetradecanylxanthate, Molybdenum pentakis-pentadecanylxanthate, Molybdenum pentakis-hexadecanylxanthate, Molybdenum pentakis-heptadecanylxanthate, Molybdenum pentakis-octadecanylxanthate, Molybdenum pentakis-nonadecanylxanthate, Molybdenum pentakis-eicosanylxanthate, and Molybdenum pentakis-decanylxanthate.

Lubricating oils and greases, for example, can be cited as lubricating compositions of this invention. The amount of a compound of this invention in a lubricating composition is the same as with the conventional friction-modifiers, for example, being compounded in a proportion with respect to the composition generally of some 0.1 to 10 wt %.

There are no particular limitations regarding the base oil or grease used in lubricating composition according to the present invention, and various conventional greases, mineral oils and synthetic oils may be conveniently used. For the purpose of this description, the term "base oil" is meant to also include a grease base stock.

The base oil used in the present invention may conveniently comprise mixtures of one or more mineral oils and/or one or more synthetic oils.

Mineral oils include liquid petroleum oils and solvent-treated or acid-treated mineral lubricating oil of the paraffinic, naphthenic, or mixed paraffinic/naphthenic type which may be further refined by hydrofinishing processes and/or dewaxing.

Suitable base oils for use in the lubricating oil composition of the present invention are Group I, Group II or Group III base oils, polyalphaolefins, Fischer-Tropsch derived base oils and mixtures thereof.

By "Group I" base oil, "Group II" base oil and "Group III" base oil in the present invention are meant lubricating oil base oils according to the definitions of American Petroleum Institute (API) categories I, II and III. Such API categories are defined in API Publication 1509, 15th Edition, Appendix E, April 2002.

Suitable Fischer-Tropsch derived base oils that may be conveniently used as the base oil in the lubricating oil composition of the present invention are those as for example disclosed in EP 0 776 959, EP 0 668 342, WO 97/21788, WO 00/15736, WO 00/14188, WO 00/14187, WO 00/14183, WO 00/14179, WO 00/08115, WO 99/41332, EP 1 029 029, WO 01/18156 and WO 01/57166.

Synthetic oils include hydrocarbon oils such as olefin oligomers (PAOs), dibasic acid esters, polyol esters, and dewaxed waxy raffinate. Synthetic hydrocarbon base oils sold by the Shell Group under the designation "XHVI" (trade mark) may be conveniently used.

Effects of the Invention (1) Novel phosphorus-free Mo-based friction-modifiers have been obtained.
(2) The compounds of this invention exhibit a low friction coefficient and they can be used as friction-modifiers for various types of energy-saving lubricating oil.
(3) The compounds of this invention are especially suitable for use as friction-modifiers for fuel-saving engine oils as they are phosphorus-free.
(4) There is no adverse effect on the catalysts (removal of NOx) which are housed in automobile exhaust gas cleaning apparatus.

EXAMPLES

The invention is described below by means of Examples, but the invention is not limited in any way by these examples.

Example 1

(The case where $R^1$ to $R^5$ are all isopropyl groups.)

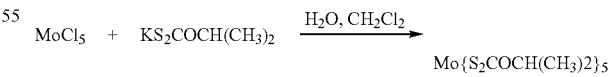

Potassium isopropylxanthate (6.38 g, 36.6 mmol) was dissolved in a solution of 20 ml of refined water and 20 ml of methylene chloride, 2 g (7.32 mmol) of molybdenum pentachloride were added slowly to the solution and the mixture was stirred for 30 minutes. The organic layer was extracted and dried with magnesium sulphate and molybdenum pentakis-isopropylxanthate, $Mo[S_2COCH(CH_3)_2]_5$, was isolated by means of column chromatography. Yield 75%

Example 2

In Example 2, $R^1$ to $R^5$ are all pentyl groups.

$$MoCl_5 + KS_2COC_5H_{11} \xrightarrow{H_2O, CH_2Cl_2} Mo\{S_2COC_5H_{11}\}_5$$

refined water and 20 ml of methylene chloride, 2 g (7.32 mmol) of molybdenum pentachloride were added slowly to the solution and the mixture was stirred for 30 minutes. The organic layer was extracted and dried with magnesium sulphate and molybdenum pentakis-pentylxanthate, $Mo[S_2COC_5H_{11}]_5$, was isolated by means of column chromatography. Yield 68%

Examples 3 and 4, and Comparative Example 1

As shown in Table 2, lubricants were prepared by adding, in Example 3 the molybdenum pentakis-isopropylxanthate obtained in Example 1, and in Example 4 the molybdenum pentakis-pentylxanthate obtained in Example 2, in such a way that the Mo content was 500 ppm in engine oil (di-isononyl adipic acid) (viscosity at 100° C.: 3.04 mm²/s) to which 5 wt % of dispersing agent (alkenylsuccinic acid polyalkylene polyimide, trade name Infineum C9266) had been added. Moreover, Comparative Example 1 was a sample of the same oil to which no friction-modifier of this invention had been added.

Figure 2:
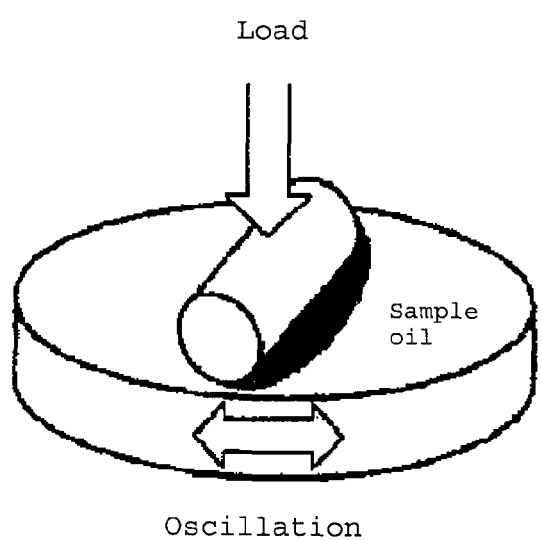
FIG. 2 is an outline drawing of the operation of the cylinder-on-disc reciprocating movement tester.

These sample oils were subjected to 30 minute friction coefficient measurement and evaluation under the conditions shown in Table 1 below using an SRV tester (a reciprocating movement tester of the cylinder-on-disc type shown in FIG. 2) and the results are shown in FIG. 1. The test piece was 52100 steel.

Testing Conditions

TABLE 1

| Condition | Parameter |
| --- | --- |
| Load | 400 N |
| Frequency | 50 Hz |
| Amplitude | 1.5 mm |
| Temperature | 100° C. |
| Sample Size | 0.5 mm³ |

TABLE 2

| | Comparative Example 1 | Example 3 | Example 4 |
| --- | --- | --- | --- |
| Base Oil | Ester Oil | Ester Oil | Ester Oil |
| Additive of this Invention | None | Compound of Example 1 500 ppm | Compound of Example 2 500 ppm |
| Alkenylsuccinic acid polyalkylene polyimide (wt %) | 5 | 5 | 5 |

The results are shown in FIG. 1.

When compared with Comparative Example 1 which did not contain a friction-modifier of this invention, Example 3 and Example 4 clearly exhibited a low friction coefficient from 1 minute after the start of the test.

What is claimed is:

1. A molybdenum alkylxanthate having general formula (1) which is indicated below General Formula (1)

$$\begin{array}{c} \phantom{R^2-CO-S-S}S-S-CO-R^3 \\ R^2-CO-S-S\diagdown\phantom{MM}\diagup S-S-CO-R^4 \\ \phantom{R^2-CO-S-SSSS}Mo \\ R^1-CO-S-S\diagup\phantom{MM}\diagdown S-S-CO-R^5 \end{array} \quad (1)$$

wherein $R^1$ to $R^5$ each represent a group individually selected from linear chain or branched alkyl groups having from 1 to 30 carbon atoms.

2. The molybdenum alkylxanthate according to claim 1, wherein $R^1$ to $R^5$ are the same alkyl group selected from the group comprising methyl, ethyl, propyl, butyl and pentyl.

3. A method comprising adding the molybdenum alkylxanthate according to claim 2 as a friction modifier to a lubricant composition.

4. A lubricating composition comprising a base oil and the molybdenum alkylxanthate according to claim 2.

5. A method of improving the friction characteristics of a lubricating composition by adding the molybdenum alkylxanthate according to claim 2.

6. A method comprising adding the molybdenum alkylxanthate according to claim 1 to a lubricant composition as a friction-modifier.

7. A lubricating composition comprising a base oil and the molybdenum alkylxanthate according to claim 1.

8. A method of improving the friction characteristics of a lubricating composition by adding the molybdenum alkylxanthate according to claim 1 to a lubricant composition.

* * * * *